United States Patent [19]
David

[11] Patent Number: 5,662,874
[45] Date of Patent: Sep. 2, 1997

[54] PREPARATION OF AMMONIUM RARE EARTH DOUBLE OXALATES AND RARE EARTH OXIDES PRODUCED THEREFROM

[75] Inventor: Claire David, Paris, France

[73] Assignee: Rhone-Poulenc Chimie, Courbevoie Cedex, France

[21] Appl. No.: 427,737

[22] Filed: Apr. 24, 1995

Related U.S. Application Data

[63] Continuation of Ser. No. 154,486, Nov. 19, 1993, abandoned, which is a continuation of Ser. No. 791,158, Nov. 13, 1991, abandoned.

[30] Foreign Application Priority Data

Nov. 13, 1990 [FR] France ............................ 90 14031

[51] Int. Cl.$^6$ ................ C01F 17/00; C07F 5/00
[52] U.S. Cl. ............................ 423/263; 534/16
[58] Field of Search ........................ 423/21.1, 263, 423/592; 534/16

[56] References Cited

U.S. PATENT DOCUMENTS

| | | | |
|---|---|---|---|
| 4,203,835 | 5/1980 | Tagashira et al. | 210/33 |
| 4,238,467 | 12/1980 | Dugan et al. | 423/263 |
| 4,375,453 | 3/1983 | Nalewajek et al. | 423/21.1 |

FOREIGN PATENT DOCUMENTS

| | | | |
|---|---|---|---|
| 2915396 | 10/1979 | Germany . | |
| 53-95911 | 8/1978 | Japan | 534/16 |
| 55-28905 | 2/1980 | Japan | 534/16 |
| 9213620 | 12/1984 | Japan | 423/263 |
| 0166222 | 8/1985 | Japan | 423/263 |
| 1183415 | 7/1989 | Japan | 423/263 |
| 2018760 | 10/1979 | United Kingdom . | |
| 2205090 | 11/1988 | United Kingdom . | |

OTHER PUBLICATIONS

Bull.Chem.Soc.Jpn., 63, 378–382, vol. 63, No. 2 *New Preparative Method of Fine Powder of Yttrium (III) Oxide by Thermal Decomposition of $NH_4Y(C_2O_4)_4.H_2O$ Fine Crystal Obtained by Reaction of a Strongly Acidic Solution of Yttrium Oxalate and an Aqueous Ammonia Solution*, by Yukinori Minagawa and Fmikazu Yajima (1990).

Bull.Chem.Soc.Jpn., 63, 2115–2117 (1990) *New Preparative Method of Fine Powder of Yttrium (III) Oxide by Thermal Decomposition of $NH_4Y(C_2O_4)_4.H_2O$ Fine Crystal Obtained by Reaction by Yttrium (III) Hydroxide Slurry with Oxalic Acid Solution*, by Yukinori Minagawa and Fmikazu Yajima.

Acta Cryst. (1967). 23,944 *The Crystal Structure of a Double Oxalate of Yttrium and Ammonium, $NH_4Y(C_2O_4)_4.H_2O$*, by T.R.R. McDonald and Jennifer M. Spink.

M.F. Barrett, et al., "Double Ammonium Oxalates of the Rare Earths and Yttrium," J. Inorg. Nucl. Chem., vol. 26, pp.931–936, 1964.

Patent Abstracts of Japan, vol. 10, No. 4, Jan. 9, 1986, & JP-A-60 166222 (Mitsubishi Kinzoku) Aug. 29, 1985.

"Gmelin Handbook of Inorganic Chemistry System", No. 39, Part D5, 1984 , Springer Verlag, Berlin RFA, p. 141.

Primary Examiner—Steven Bos
Attorney, Agent, or Firm—Burns, Doane, Swecker & Mathis, L.L.P.

[57] ABSTRACT

Particulate ammonium rare earth double oxalate crystals, homogeneous in particle size and having a narrow particle size distribution and readily converted into rare earth oxide particles by simple calcination, e.g., yttrium oxide particles, are prepared by (a) intimately admixing, in an aqueous medium, (i) at least one precursor compound adapted to liberate oxalate ions in aqueous solution with (ii) at least one water-soluble rare earth compound and (iii) at least one ammonium salt, (b) separating the double oxalate precipitate thus formed, and (c), optionally, washing and drying such double oxalate precipitate.

18 Claims, 1 Drawing Sheet

1

PREPARATION OF AMMONIUM RARE EARTH DOUBLE OXALATES AND RARE EARTH OXIDES PRODUCED THEREFROM

This application is a continuation of application Ser. No. 08/154,486, filed Nov. 19, 1993, now abandoned, which is a continuation of application Ser. No. 07/791,158, filed Nov. 13, 1991, now abandoned.

CROSS REFERENCE TO COMPANION APPLICATION

My copending application Ser. No. 07/791,206, now abandoned is filed concurrently herewith and assigned to the assignee hereof.

BACKGROUND OF THE INVENTION

1. Field of the Invention

The present invention relates to the preparation of ammonium rare earth double oxalates, and to the conversion of the double oxalates thus prepared into rare earth oxides.

This invention especially relates to the preparation of such double oxalates possessing a controlled and specific morphology and particle size.

2. Description of the Prior Art

The rare earth oxides find numerous applications in such fields as, in particular, ceramics and electronics, but, at the present time, an increasing demand exists for products having controlled particle size.

One of the convention processes for preparing rare earth oxides, and which is amply described in the literature, in particular in the *Nouveau Traits De Chimie Minerale* ("New Treatise on Inorganic Chemistry"), Volume VII, (1959), p. 1007 by Paul Pascal, entails calcining at temperatures ranging from 500° to 900° C. the rare earth oxalates prepared by precipitation, using oxalic acid, of rare earth salts in the form of an aqueous solution thereof. However, such a process produces only rare earth oxides possessing coarse particle sizes.

It is also known to this art, per JP 53/095,911-A (Chemical Abstracts, 90, 40940 w), to prepare finely divided rare earth oxides, and more especially finely divided yttrium oxide, by calcination of an ammonium/yttrium oxalate. This process comprises precipitating the yttrium in the form of its hydroxide from an aqueous solution of a yttrium salt. The aqueous solution of the yttrium salt is reacted with a basic aqueous solution such as ammonia solution, and the resulting hydroxide slurry is then treated with oxalic acid, and, finally, the resulting precipitate is separated, washed and calcined at a temperature of 750° C. According to said JP 53/095911-A, a finely divided yttrium oxide is produced. Its particle diameter ranges from 0.9 to 4.5 µm, the crystals having the shape of small plates with rounded edges.

However, control of the particle size, as well as of the particle size distribution, are relatively difficult, since these are greatly influenced by the conditions of actually carrying out such process.

SUMMARY OF THE INVENTION

Accordingly, a major object of the present invention is the provision of an improved process for the preparation of ammonium rare earth double oxalates having a narrow particle size distribution, with average crystal sizes which can be controlled, and which improved process otherwise avoids the above disadvantages and drawbacks to date characterizing the state of this art.

By "ammonium rare earth double oxalate" is intended a compound comprising one or more rare earths combined with ammonium and oxalate ions and which is converted into simple or mixed oxides by calcination.

By the term "rare earths" are intended the elements of the Periodic Table having atomic numbers ranging from 57 to 71, inclusive, belonging to the lanthanide family, as well as yttrium having an atomic number of 39.

Briefly, the present invention features a process for the preparation of an ammonium rare earth double oxalate, comprising admixing, in an aqueous medium, at least one precursor compound adapted to liberate oxalate ions in solution with at least one water-soluble rare earth (RE) compound and one ammonium salt, separating the precipitate thus formed, and, optionally, drying said precipitate.

BRIEF DESCRIPTION OF THE DRAWING

The FIGURE of Drawing is a photomicrograph (6,000× magnification) of yttrium oxide crystals produced from an ammonium/yttrium double oxalate prepared according to the process of the invention.

DETAILED DESCRIPTION OF THE PREFERRED EMBODIMENTS OF THE INVENTION

Figure 1:
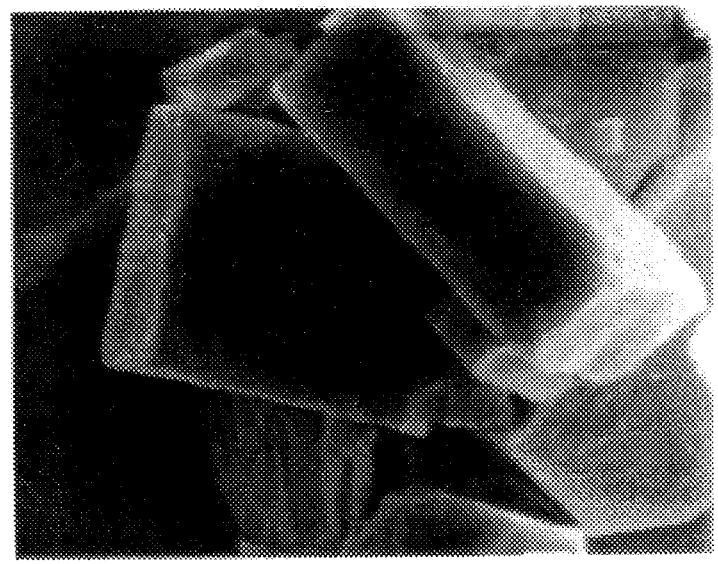

More particularly according to the present invention, the starting material ammonium salt is advantageously ammonium nitrate, ammonium chloride or ammonium acetate.

Thus, an ammonium salt such as, for example, ammonium nitrate, which is the preferred compound of the invention, permits better control of the precipitation of the double oxalate, since it precipitates directly without prior precipitation of the rare earth hydroxide as in the prior art process discussed above. This direct precipitation permits the particle size and the distribution of crystallite sizes of the precipitated double oxalate to be controlled.

In a first preferred embodiment of the invention, the ammonium salt and the rare earth compound are intimately admixed in an aqueous medium to form a first solution.

In this embodiment, the compound capable of liberating oxalate ions in solution is added to the first solution.

The state or concentration of this compound permits the size of the crystallites of precipitated double oxalate, as well as their particle size distribution, to be modified and controlled.

Advantageously, the compound adapted to liberate oxalate ions is selected from among oxalic acid, crystallized or in solution, alkali metal oxalates, crystallized or in solution, and the like.

Thus, addition of the compound adapted to liberate oxalate ions in solid form produces a precipitate of small-sized crystallites, for example on the order of 1 to 4 µm, while addition of this compound in the form of an aqueous solution, thereby forming a second solution, produces larger crystallite sizes.

In a second preferred embodiment of the invention, the first solution containing an ammonium salt and a rare earth compound is added to the second solution containing the compound adapted to liberate oxalate ions.

However, in this embodiment, the rare earth compound and the ammonium salt may be added in the form of a solution or in crystallized form. These compounds may be added either in the form of a solid mixture or of a common solution, or in separate form, but they should then preferably be added simultaneously to the second solution.

Exemplary rare earth compounds which are well suited to carry out the invention include the nitrates, chlorides and sulfates, or a mixture of rare earth salts, with the nitrates being the preferred compounds of the invention.

Among these compounds, yttrium nitrate, europium nitrate, lanthanum nitrate, neodymium nitrate, dysprosium nitrate, cerium nitrate, gadolinium nitrate, terbium nitrate or a mixture of these are preferred.

In particular, it is possible to employ an aqueous solution containing rare earth salts which originates directly or indirectly from the processing of rare earth ores.

Although the process of the invention applies perfectly well to the cerium rare earths, it is more especially applicable to the yttrium rare earths.

By "cerium rare earths" are intended the lighter rare earth elements beginning with lanthanum and extending up to neodymium according to atomic number, and by "yttrium rare earths" are intended the heavier rare earth elements according to atomic number, beginning with samarium and extending to lutetium, but including yttrium.

The concentration of the rare earth compound is not critical.

According to another preferred embodiment of the process of the invention, the $C_2O_4^=/RE$ and $NH_4^+/RE$ mole ratios upon completion of the precipitation are not less than 2, and preferably not less than 2.5.

However, the concentration of $(C_2O_4)^=$ and $NH_4^+$ ions in the solutions is not critical and can vary over wide limits.

In another preferred embodiment of the invention, the oxalate concentrations, as well as the rare earth and ammonium ion concentration in the different solutions and the volumes of the first and second solutions, as well as the amounts of crystallized materials added, will be determined such as to provide in the final reaction medium a mole ratio of oxalate ion to rare earths $((C_2O_4)^=/RE)$ of not less than 2, and advantageously not less than 2.5, and a ratio of ammonium to rare earths $(NH_4^+/RE)$ of not less than 2, and preferably not less than 2.5.

The actual conditions for carrying out the process of the invention are essentially uncritical for producing a double oxalate. Nevertheless, control of the rate of mixing of the different solutions or the rate of introduction of the crystallized materials into the solutions, of temperature and of the stirring of the mixture permits the morphology of the precipitated double oxalate to be modified and controlled.

Moreover, the temperature exerts an influence on the precipitation yield, since the solubility coefficient of the double oxalate increases with an increase in temperature.

In another preferred embodiment of the invention, the precipitation is carried out at a temperature ranging from 30° C. to 90° C., and preferably from 35° C. to 70° C.

In yet another preferred embodiment of the invention, the separation of the precipitate is carried out between about 5 min and 2 hours after completion of precipitation. During this period, the reaction medium may be maintained under stirring or otherwise.

This step permits a rearrangement of the crystals and is generally referred to as "aging" of the precipitate.

The precipitate obtained is separated from the supernatant liquid by any solid/liquid separation technique, such as, for example, filtration, centrifugation, decantation, or the like. It may also be subjected to one or more washings in order, for example, to remove soluble salts.

The ammonium rare earth double oxalate can be subjected to drying in order to evaporate unbound water, for example by thermal treatment at a temperature ranging from 50° C. to 100° C. or by drying under reduced pressure.

The process of the invention produces an ammonium rare earth double oxalate having a homogeneous particle size, as well as a very narrow particle size distribution of the crystals.

The crystals range, for example, from about 1 to 4 µm in size, and have the shape of a small plate.

One use of these ammonium rare earth double oxalates is for the production of rare earth oxides by thermal decomposition of such oxalates.

The morphology and particle size of the rare earth oxides produced by decomposition of a double oxalate is generally similar to that of the precursor or starting material double oxalate. However, depending on the conditions of thermal treatment of the double oxalate, the particle size of the oxide may be slightly different from that of the oxalate.

The thermal treatment or calcination is generally carried out at a temperature ranging from 600° C. to 1,200° C., and advantageously from 800° C. to 1,000° C.

The calcination time is determined in conventional manner by monitoring for constant weight. For example, the calcination time can range from about 30 minutes to 6 hours.

In order to further illustrate the present invention and the advantages thereof, the following specific examples are given, it being understood that same are intended only as illustrative and in nowise limitative.

EXAMPLE 1

A solution containing yttrium nitrate at a concentration of 1.36 mol/l was mixed with a 2M ammonium nitrate solution to provide an $NH_4^+/Y$ ratio=5.

This solution was heated to 45° C. 85 g of crystallized oxalic acid were added, this resulting in a $(C_2O_4)^=/Y$ ratio= 2.5.

The mixture was maintained under stirring for one hour at this temperature.

The precipitate was then recovered by filtration and washed with water.

The washed precipitate was dried at 100° C. and then subjected to X-ray analysis to confirm its ammonium/ yttrium double oxalate structure.

This salt was converted to the oxide by calcination at 900° C. for 1 hour.

Particle size analysis carried out by means of a CILAS® granulometer demonstrated that the oxide possessed a mean particle diameter of 2.5 µm, with a particle size dispersion factor $$\frac{\sigma}{m}$$

of 0.53.

The factor $$\frac{\sigma}{m}$$

was calculated by the formula:

$$\frac{\sigma}{m} = \frac{\phi_{84} - \phi_{16}}{\phi_{50}}$$

in which $\phi_{84}$ is the diameter for which 84% of the particles have a diameter not exceeding $\Phi_{84}$, $\phi_{16}$ is the diameter for which 16% of the particles have a diameter not exceeding $\Phi_{16}$, and $\phi_{50}$ is the mean particle diameter.

EXAMPLE 2

Following the procedure of Example 1, a solution was prepared containing yttrium nitrate and ammonium nitrate with an $NH_4^+/Y$ ratio=3.90.

To this solution after, heating same to 45° C., a 1M solution of oxalic acid was added such as to provide a $C_2O_4^=/Y$ ratio=2.

The reaction medium was then maintained under stirring for 30 minutes.

After filtration and washing with water, the precipitate was dried at 100° C. and then calcined at 900° C. to convert it to yttrium oxide.

Particle size analysis of this oxide demonstrated that it had a mean diameter $\phi_{50}$ equal to 13.6 μm and a $$\frac{\sigma}{m}$$

equal to 0.51.

The crystals of this oxide are illustrated in the accompanying single FIGURE of Drawing (magnification 6,000 times).

EXAMPLE 3

A solution containing 0.675 mol of crystallized oxalic acid was heated to 45° C.

To this solution, a second solution containing an ammonium nitrate and an yttrium nitrate was added to provide the following ratios in the reaction medium:

$C_2O_4^=/Y=2.5$ $NH_4^+/Y=4.96$

The mixture was maintained under stirring for 1 hour and the precipitate was then filtered off and washed with water.

After drying at 100° C., the double oxalate was calcined for 1 hour at 900° C.

Particle size analysis demonstrated that it had a $\phi_{50}$ equal to 4.06 μm and a $$\frac{\sigma}{m} = 0.48.$$

EXAMPLE 4

To a solution of oxalic acid heated to 60° C., a solution of yttrium nitrate and a solution of ammonium nitrate were added simultaneously such as to provide the following ratios in the reaction medium:

$C_2O_4^==2.5$ $NH_4^+/Y=5.15$

The mixture was maintained under stirring for one hour.

The precipitate was then filtered off and washed with water, thereafter dried and calcined as in the previous examples.

The oxide thereby obtained possessed a mean particle diameter equal to 3 μm and a $$\frac{\sigma}{m}$$

equal to 0.6.

EXAMPLE 5

The procedure of Example 1 was repeated, except that a solution of yttrium chloride and ammonium chloride was used in place of the solution of yttrium nitrate and ammonium nitrate.

The ratios of the species in the reaction medium were:

$C_2O_4^=/Y=2.54$ $NH_4^+/Y=3.26$

The yttrium oxide obtained by calcination of the precipitate, recovered according to the technique described in the previous examples, possessed a mean particle diameter equal to 3.5 μm and a $$\frac{\sigma}{m} = 0.56.$$

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an ammonium rare earth double oxalate, comprising (a) intimately admixing, in an aqueous medium, (i) at least one precursor compound capable of liberating oxalate ions in aqueous solution with (ii) at least one water-soluble rare earth compound containing a rare earth metal having an atomic number of 39 or ranging from 57 to 71 and (iii) at least one ammonium salt to form an ammonium rare earth double oxalate precipitate, (b) separating the double oxalate precipitate thus formed, and (c), optionally, washing and drying said double oxalate precipitate; wherein the double oxalate precipitate is precipitated without prior precipitation of a rare earth hydroxide and said compound (i), compound (ii) and salt (iii) are different from each other, and wherein said ammonium salt comprises ammonium nitrate, ammonium chloride or ammonium acetate.

2. The process as defined by claim 1, comprising dissolving said at least one water-soluble rare earth compound and said ammonium salt in said aqueous medium and adding thereto said at least one precursor compound capable of liberating oxalate ions.

3. The process as defined by claim 1, said at least one precursor compound capable of liberating oxalate ions comprising oxalic acid or an alkali metal oxalate.

4. The process as defined by claim 1, comprising dissolving said at least one water-soluble rare earth compound and said ammonium salt in said aqueous medium to form a first aqueous solution, dissolving said at least one precursor compound capable of liberating oxalate ions in water to form a second aqueous solution, and adding said first aqueous solution to said second aqueous solution.

5. The process as defined by claim 1, said at least one water-soluble rare earth compound comprising a rare earth salt.

6. The process as defined by claim 5, said rare earth salt comprising a nitrate, chloride, sulfate or mixture thereof.

7. The process as defined by claim 5, said at least one water-soluble rare earth compound comprising yttrium nitrate, europium nitrate, lanthanum nitrate, neodymium nitrate, dysprosium nitrate, cerium nitrate, gadolinium nitrate or terbium nitrate, or mixture thereof.

8. The process as defined by claim 1, wherein $C_2O_4^=/RE$ and $NH_4^+/RE$ mole ratios upon completion of precipitation are not less than 2.

9. The process as defined by claim 8, said mole ratios being not less than 2.5.

10. The process as defined by claim 1, said precipitate being formed at a temperature ranging from 30° C. to 90° C.

11. The process as defined by claim 10, said precipitate being formed at a temperature ranging from 35° C. to 70° C.

12. The process as defined by claim 1, comprising separating said double oxalate precipitate from 5 minutes to 2 hours after completion of precipitation.

13. Uncalcined, precipitated crystals of an ammonium rare earth double oxalate having a platelet shape and a mean particle size of 1–4 μm prepared by the process according to claim 1.

14. A process for the preparation of a particulate rare earth oxide, comprising calcining particulate ammonium rare earth double oxalate crystals prepared by (a) intimately admixing, in an aqueous medium, (i) at least one precursor compound capable of liberating oxalate ions in aqueous solution with (ii) at least one water-soluble rare earth compound containing a rare earth metal having an atomic number of 39 or ranging from 57 to 71 and (iii) at least one ammonium salt to form an ammonium rare earth double oxalate precipitate, (b) separating the double oxalate precipitate thus formed, and (c) optionally, washing and drying said double oxalate precipitate; wherein the double oxalate precipitate is precipitated without prior precipitation of a rare earth hydroxide and said compound (i), compound (ii) and salt (iii) are different from each other, and wherein said ammonium salt comprises ammonium nitrate, ammonium chloride or ammonium acetate.

15. The process as defined by claim 14, comprising calcining at a temperature ranging from 600° C. to 1,200° C.

16. Calcined, precipitated particulates of a rare earth oxide having a mean particle size of 1–4 μm and a particle size dispersion factor of less than or equal to 0.6 prepared by the process according to claim 14.

17. A process for preparing ammonium rare earth double oxalate crystals comprising (a) intimately admixing, in an aqueous medium, (i) at least one precursor compound capable of liberating oxalate ions in aqueous solution with (ii) at least one water-soluble rare earth compound containing a rare earth metal having an atomic number of 39 or ranging from 57 to 71 and (iii) at least one ammonium salt to form crystals of an ammonium rare earth double oxalate having a mean particle size of 1–4 μm, (b) separating the double oxalate crystals thus formed, and (c) optionally, washing and drying said double oxalate crystals; wherein the double oxalate crystals are precipitated without prior precipitation of a rare earth hydroxide and said compound (i), compound (ii) and salt (iii) are different from each other, and wherein said ammonium salt comprises ammonium nitrate, ammonium chloride or ammonium acetate.

18. The process according to claim 17, further comprising calcining said crystals having a mean particle size of 1–4 μm to produce particulates of a rare earth oxide having a mean particle size of 1–4 μm and a particle size dispersion factor of less than or equal to 0.6.

* * * * *